United States Patent [19]

Wölfel et al.

[11] Patent Number: 5,843,687
[45] Date of Patent: Dec. 1, 1998

[54] ISOLATED, TYROSINASE DERIVED PEPTIDES AND USES THEREOF

[75] Inventors: Thomas Wölfel, Mainz, Germany; Aline Van Pel, Brussels, Belgium; Vincent Brichard, Brussels, Belgium; Thierry Boon-Falleur, Brussels, Belgium

[73] Assignee: Ludwig Institute for Cancer Research, New York, N.Y.

[21] Appl. No.: 545,212

[22] Filed: Oct. 19, 1995

Related U.S. Application Data

[60] Division of Ser. No. 233,305, Apr. 26, 1994, Pat. No. 5,519,117, which is a continuation-in-part of Ser. No. 203,054, Feb. 28, 1994, Pat. No. 5,530,096, which is a continuation-in-part of Ser. No. 81,673, Jun. 23, 1993, Pat. No. 5,487,974, which is a continuation-in-part of Ser. No. 54,714, Apr. 28, 1993, which is a continuation-in-part of Ser. No. 994,928, Dec. 22, 1992, abandoned.

[51] Int. Cl.⁶ .................. G01N 33/53; A61K 39/385; A61K 38/04
[52] U.S. Cl. .................. 435/7.24; 424/193.1; 530/328
[58] Field of Search ................. 435/7.24; 424/193.1; 530/328

[56] References Cited

U.S. PATENT DOCUMENTS 4,898,814  2/1990  Kwon ........................................ 435/6

OTHER PUBLICATIONS van der Bruggen et al., A gene encoding an antigen recognized by cytolytic T lymphocytes, on a human melanoma, Sci. 254: 1643–1647, see Abstracat, p. 1643, col. 1, third sentence, second paragraph, Dec. 1991.

Ruppert et al., Multiple transcripts of the mouse tyrosinase gene are generated by alternative, splicing, The EMBO J. vol. 7, No. 9, pp. 2715–2722, p. 2715, col. 1, lines 5–7, Jun. 1988.

Traversari, et al., Transfection and expression of a gene coding for a human melanoma antigen recognized by autologous cytolyic T lymphocytes, Immunogenetics 35: 145–152, Abstract, first sentence, p. 146, col. 2, "CTL clones", p. 147, col. 1, Sc, 1992.

Brichard, et al, "The Tyrosinase Gene Codes for an Antigen–Recognized by Autologous Cytolytic T Lymphocytes on HLA–A2 Melanomas", J. Exp. Med. 178: 489–495 (1993).

Coulie, et al, "Genes Coding For Tumor Antigens Recognized by Human Cytolytic T Lymphocytes", J. Immunotherapy 14: 104–109 (1993).

Slingluff, et al, "Recognition of Human Melanoma Cells by HLA–A2.1 Restricted Cytotoxic T Lymphocytes As Mediated By At Least Six Shared Peptide Epitopes", J. Immunol. 150(7): 2955–2963 (Apr. 1, 1993).

Barinaga "Getting Some 'Backbone': How MHC Binds Peptides" Science 257: 880–881 (August 14, 1992).

Falk, et al, "Allele Specific Motifs revealed by sequencing of self–peptides eluted from MHC molecules", Nature 351: 290–296 (May 23, 1991).

Wolfel, et al, "Lysis of Human Melanoma Cells by Autologous Cytolytic T Cells Clones", J. Exp. Med. 170: 797–810 (Sep. 1989).

*Primary Examiner*—Ponnathapura Achutamurthy
*Assistant Examiner*—Hankyel T. Park
*Attorney, Agent, or Firm*—Felfe & Lynch

[57] ABSTRACT

The invention relates to the identification of complexes of human leukocyte antigen molecules and tyrosinase derived peptides on the surfaces of abnormal cells. The therapeutic and diagnostic ramifications of this observation are the subject of the invention.

7 Claims, 12 Drawing Sheets

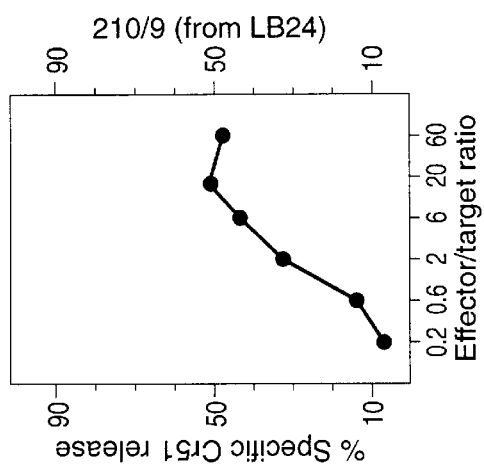
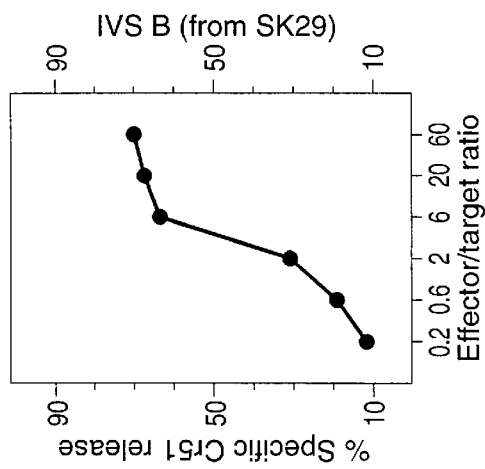
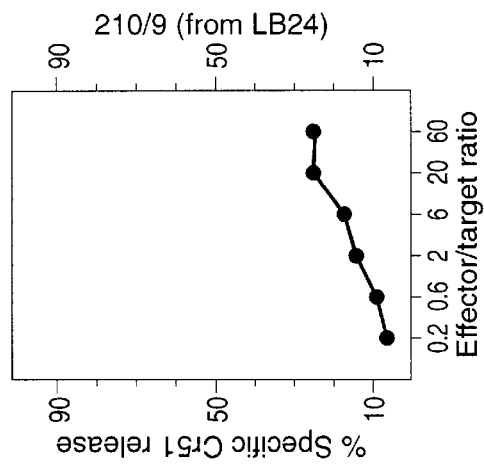
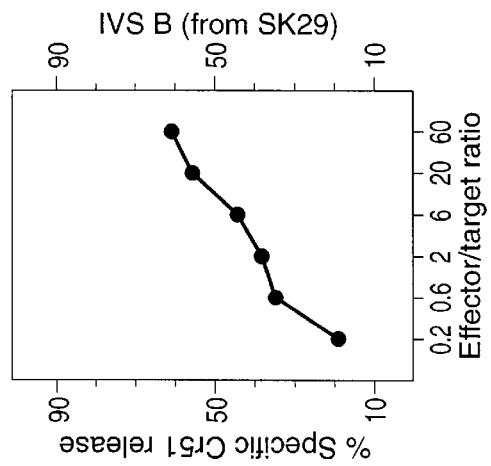
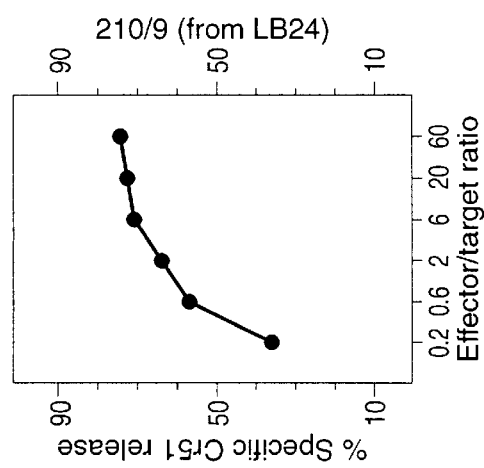
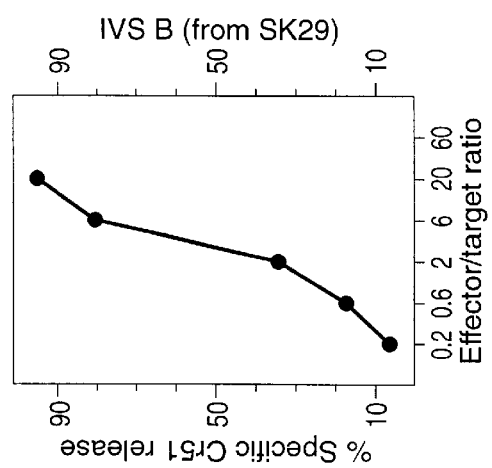

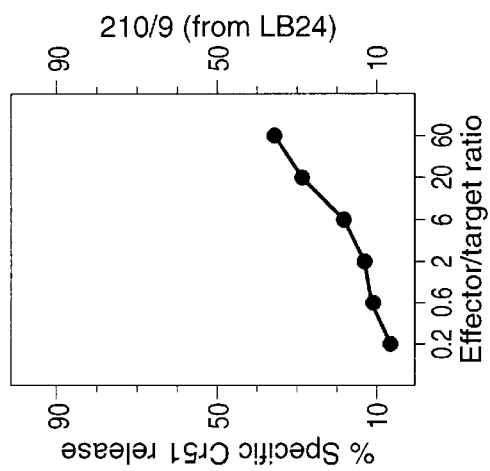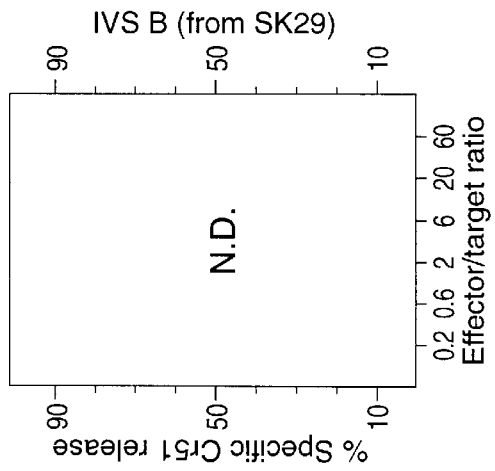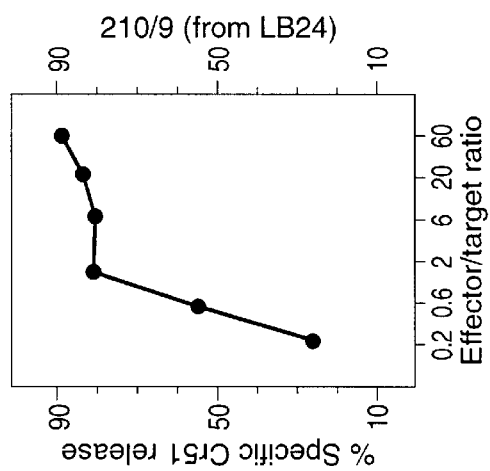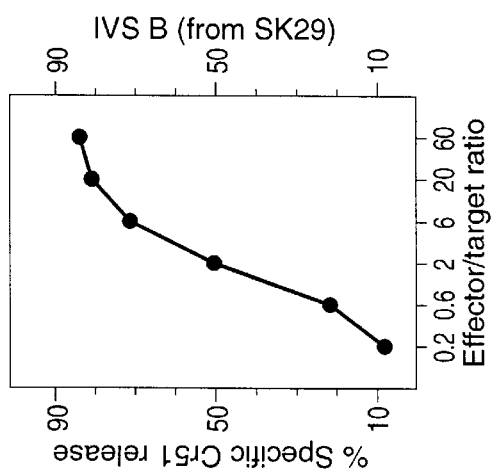

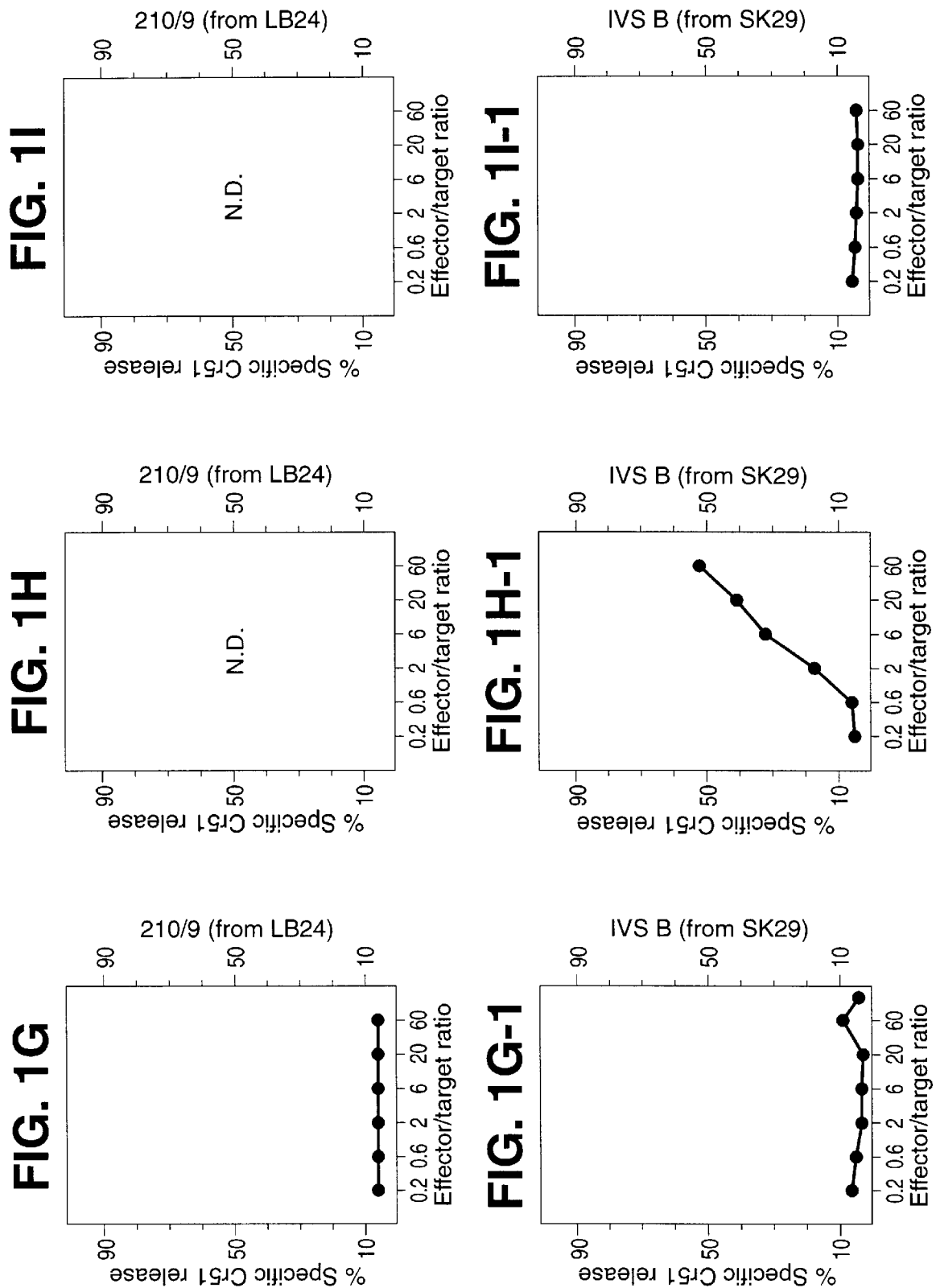

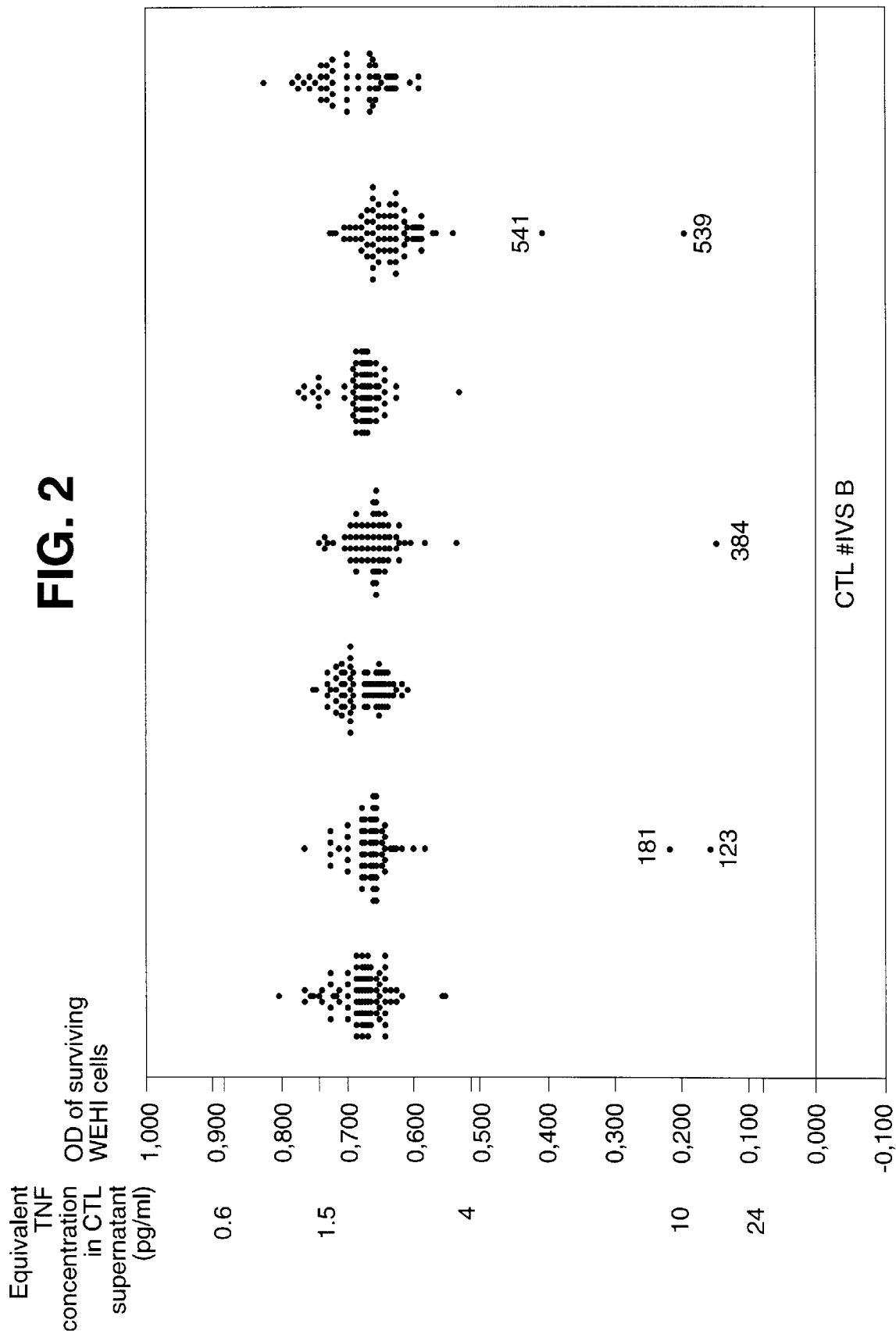

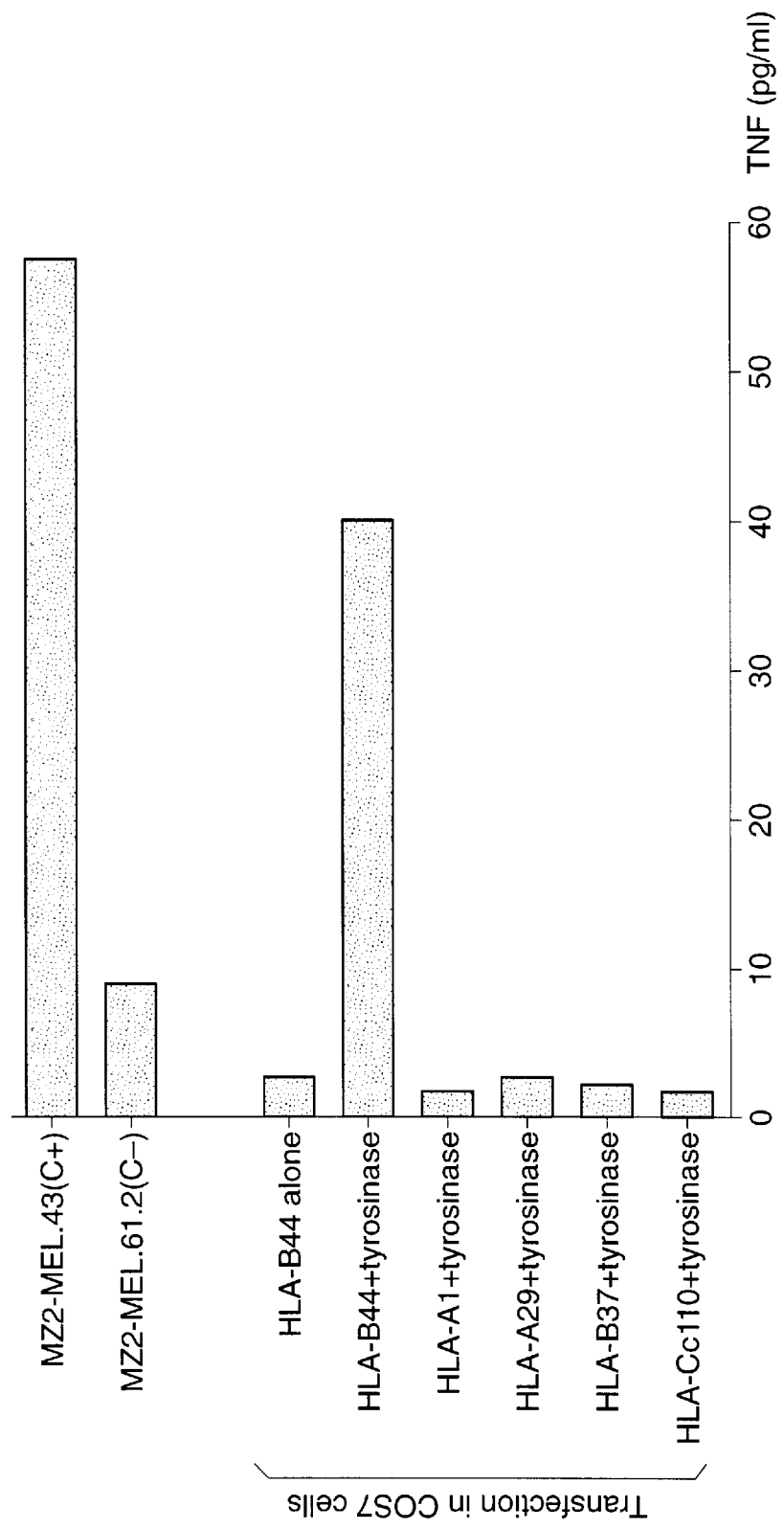

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 1894 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GGA  AGA  ATG  CTC  CTG  GCT  GTT  TTG  TAC  TGC  CTG  CTG  TGG  AGT  TTC  CAG         48
Gly  Arg  Met  Leu  Leu  Ala  Val  Leu  Tyr  Cys  Leu  Leu  Trp  Ser  Phe  Gln
          -15                      -10                           -5

ACC  TCC  GCT  GGC  CAT  TTC  CCT  AGA  GCC  TGT  GTC  TCC  TCT  AAG  AAC  CTG         96
Thr  Ser  Ala  Gly  His  Phe  Pro  Arg  Ala  Cys  Val  Ser  Ser  Lys  Asn  Leu
               1              5                        10

ATG  GAG  AAG  GAA  TGC  TGT  CCA  CCG  TGG  AGC  GGG  GAC  AGG  AGT  CCC  TGT        144
Met  Glu  Lys  Glu  Cys  Cys  Pro  Pro  Trp  Ser  Gly  Asp  Arg  Ser  Pro  Cys
15                       20                       25                       30

GGC  CAG  CTT  TCA  GGC  AGA  GGT  TCC  TGT  CAG  AAT  ATC  CTT  CTG  TCC  AAT        192
Gly  Gln  Leu  Ser  Gly  Arg  Gly  Ser  Cys  Gln  Asn  Ile  Leu  Leu  Ser  Asn
                    35                       40                       45

GCA  CCA  CTT  GGG  CCT  CAA  TTT  CCC  TTC  ACA  GGG  GTG  GAT  GAC  CGG  GAG        240
Ala  Pro  Leu  Gly  Pro  Gln  Phe  Pro  Phe  Thr  Gly  Val  Asp  Asp  Arg  Glu
               50                       55                       60

TCG  TGG  CCT  TCC  GTC  TTT  TAT  AAT  AGG  ACC  TGC  CAG  TGC  TCT  GGC  AAC        288
Ser  Trp  Pro  Ser  Val  Phe  Tyr  Asn  Arg  Thr  Cys  Gln  Cys  Ser  Gly  Asn
          65                       70                       75

TTC  ATG  GGA  TTC  AAC  TGT  GGA  AAC  TGC  AAG  TTT  GGC  TTT  TGG  GGA  CCA        336
Phe  Met  Gly  Phe  Asn  Cys  Gly  Asn  Cys  Lys  Phe  Gly  Phe  Trp  Gly  Pro
     80                       85                       90

AAC  TGC  ACA  GAG  AGA  CGA  CTC  TTG  GTG  AGA  AGA  AAC  ATC  TTC  GAT  TTG        384
Asn  Cys  Thr  Glu  Arg  Arg  Leu  Leu  Val  Arg  Arg  Asn  Ile  Phe  Asp  Leu
95                       100                      105                      110

AGT  GCC  CCA  GAG  AAG  GAC  AAA  TTT  TTT  GCC  TAC  CTC  ACT  TTA  GCA  AAG        432
Ser  Ala  Pro  Glu  Lys  Asp  Lys  Phe  Phe  Ala  Tyr  Leu  Thr  Leu  Ala  Lys
                    115                      120                      125

CAT  ACC  ATC  AGC  TCA  GAC  TAT  GTC  ATC  CCC  ATA  GGG  ACC  TAT  GGC  CAA        480
His  Thr  Ile  Ser  Ser  Asp  Tyr  Val  Ile  Pro  Ile  Gly  Thr  Tyr  Gly  Gln
               130                      135                      140

ATG  AAA  AAT  GGA  TCA  ACA  CCC  ATG  TTT  AAC  GAC  ATC  AAT  ATT  TAT  GAC        528
Met  Lys  Asn  Gly  Ser  Thr  Pro  Met  Phe  Asn  Asp  Ile  Asn  Ile  Tyr  Asp
     145                      150                      155

CTC  TTT  GTC  TGG  ATG  CAT  TAT  TAT  GTG  TCA  ATG  GAT  GCA  CTG  CTT  GGG        576
Leu  Phe  Val  Trp  Ile  His  Tyr  Tyr  Val  Ser  Met  Asp  Ala  Leu  Leu  Gly
     160                      165                      170

GGA  TCT  GAA  ATC  TGG  AGA  GAC  ATT  GAT  TTT  GCC  CAT  GAA  GCA  CCA  GCT        624
Gly  Tyr  Glu  Ile  Trp  Arg  Asp  Ile  Asp  Phe  Ala  His  Glu  Ala  Pro  Ala
175                      180                      185                      190

TTT  CTG  CCT  TGG  CAT  AGA  CTC  TTC  TTG  CGG  TGG  GAA  CAA  GAA  ATC        672
Phe  Leu  Pro  Trp  His  Arg  Leu  Phe  Leu  Leu  Arg  Trp  Glu  Gln  Gly  Ile
                    195                      200                      205

CAG  AAG  CTG  ACA  GGA  GAT  GAA  AAC  TTC  ACT  ATT  CCA  TAT  TGG  GAC  TGG        720
Gln  Lys  Leu  Thr  Gly  Asp  Glu  Asn  Phe  Thr  Ile  Pro  Tyr  Trp  Asp  Trp
               210                      215                      220

CGG  GAT  GCA  GAA  AAG  TGT  GAC  ATT  TGC  ACA  GAT  GAG  TAC  ATG  GGA  GGT        768
Arg  Asp  Ala  Glu  Lys  Cys  Asp  Ile  Cys  Thr  Asp  Glu  Tyr  Met  Gly  Gly
               225                      230                      235

CAG  CAC  CCC  ACA  AAT  CCT  AAC  TTA  CTC  AGC  CCA  GCA  TCA  TTC  TTC  TCC        816
Gln  His  Pro  Thr  Asn  Pro  Asn  Leu  Leu  Ser  Pro  Ala  Ser  Phe  Phe  Ser
     240                      245                      250

TCT  TGG  CAG  ATT  GTC  TGT  AGC  CGA  TTG  GAG  GAG  TAC  AAC  AGC  CAT  CAG        864
Ser  Trp  Gln  Ile  Val  Cys  Ser  Arg  Leu  Glu  Glu  Tyr  Asn  Ser  His  Gln
```

```
                  255                        260                        265                        270
TCT  TTA  TGC  AAT  GGA  ACG  CCC  GAG  GGA  CCT  TTA  CGG  CGT  AAT  CCT  GGA              912
Ser  Leu  Cys  Asn  Gly  Thr  Pro  Glu  Gly  Pro  Leu  Arg  Arg  Asn  Pro  Gly
                    275                       280                       285

AAC  CAT  GAC  AAA  TCC  AGA  ACC  CCA  AGG  CTC  CCC  TCT  TCA  GCT  GAT  GTA              960
Asn  His  Asp  Lys  Ser  Arg  Thr  Pro  Arg  Leu  Pro  Ser  Ser  Ala  Asp  Val
               290                            295                      300

GAA  TTT  TGC  CTG  AGT  TTG  ACC  CAA  TAT  GAA  TCT  GGT  TCC  ATG  GAT  AAA             1008
Glu  Phe  Cys  Leu  Ser  Leu  Thr  Gln  Tyr  Glu  Ser  Gly  Ser  Met  Asp  Lys
               305                            310                 315

GCT  GCC  AAT  TTC  AGC  TTT  AGA  AAT  ACA  CTG  GAA  GGA  TTT  GCT  AGT  CCA             1056
Ala  Ala  Asn  Phe  Ser  Phe  Arg  Asn  Thr  Leu  Glu  Gly  Phe  Als  Ser  Pro
          320                            325                      330

CTT  ACT  GGG  ATA  GCG  GAT  GCC  TCT  CAA  AGC  AGC  ATG  CAC  AAT  GCC  TTG             1104
Leu  Thr  Gly  Ile  Ala  Asp  Ala  Ser  Gln  Ser  Ser  Met  His  Asn  Ala  Leu
335                           340                      345                      350

CAC  ATC  TAT  ATG  AAT  GGA  ACA  ATG  TCC  CAG  GTA  CAG  GGA  TCT  GCC  AAC             1152
His  Ile  Tyr  Met  Asn  Gly  Thr  Met  Ser  Gln  Met  Gln  Gly  Ser  Ala  Asn
                         355                      360                      365

GAT  CCT  ATC  TTC  CTT  CTT  CAC  CAT  GCA  TTT  GTT  GAC  AGT  ATT  TTT  GAG             1200
Asp  Pro  Ile  Phe  Leu  Leu  His  His  Ala  Phe  Val  Asp  Ser  Ile  Phe  Glu
                    370                       375                 380

CAG  TGG  CTC  CAA  AGG  CAC  CGT  CCT  CTT  CAA  GAA  GTT  TAT  CCA  GAA  GCC             1248
Gln  Trp  Leu  Arg  Arg  His  Arg  Pro  Leu  Gln  Glu  Val  Tyr  Pro  Glu  Ala
               385                            390                 395

AAT  GCA  CCC  ATT  GGA  CAT  AAC  CGG  GAA  TCC  TAC  ATG  GTT  CCT  TTT  ATA             1296
Asn  Ala  Pro  Ile  Gly  His  Asn  Arg  Glu  Ser  Tyr  Met  Val  Pro  Phe  Ile
          400                            405                 410

CCA  CTG  TAC  AGA  AAT  GGT  GAT  TTC  TTT  ATT  TCA  TCC  AAA  GAT  CTG  GGC             1344
Pro  Leu  Tyr  Arg  Asn  Gly  Asp  Phe  Phe  Ile  Ser  Ser  Lys  Asp  Leu  Gly
415                           420                      425                      430

TAT  GAC  TAT  AGC  TAT  CTA  CAA  GAT  TCA  GAC  CCA  GAC  TCT  TTT  CAA  GAC             1392
Tyr  Asp  Tyr  Ser  Tyr  Leu  Gln  Asp  Ser  Asp  Pro  Asp  Ser  Phe  Gln  Asp
                         435                      440                      445

TAC  ATT  AAG  TCC  TAT  TTG  GAA  CAA  GCG  AGT  CGG  ATC  TGG  TCA  TGG  CTC             1440
Tyr  Ile  Lys  Ser  Tyr  Leu  Gly  Gln  Ala  Ser  Arg  Ile  Trp  Ser  Trp  Leu
               450                            455                 460

CTT  GGG  GCG  GCG  ATG  GTA  GGG  GCC  GTC  CTC  ACT  GCC  CTG  CTG  GCA  GGG             1488
Leu  Gly  Ala  Ala  Met  Val  Gly  Ala  Val  Leu  Thr  Ala  Leu  Leu  Ala  Gly
          465                            470                 475

CTT  GTG  AGC  TTG  CTG  TGT  CGT  CAC  AAG  AGA  AAG  CAG  CTT  CCT  GAA  GAA             1536
Leu  Val  Ser  Leu  Leu  Cys  Arg  His  Lys  Arg  Lys  Gln  Leu  Pro  Glu  Glu
          480                            485                 490

AAG  CAG  CCA  CTC  CTC  ATG  GAG  AAA  GAG  GAT  TAC  CAC  AGC  TTG  TAT  CAG             1584
Lys  Gln  Pro  Leu  Leu  Met  Glu  Lys  Glu  Asp  Tyr  His  Ser  Leu  Tyr  Gln
495                      500                            505                 510

AGC  CAT  TTA                                                                                1593
Ser  His  Leu
          513

TAAAAGGCTT  AGGCAATAGA  GTAGGGCCAA  AAAGCCTGAC  CTCACTCTAA  CTCAAAGTAA                      1653

TGTCCAGGTT  CCCAGAGAAT  ATCTGCTGGT  ATTTTTCTGT  AAAGACCATT  TGCAAAATTG                      1713

TAACCTAATA  CAAAGTGTAG  CCTTCTTCCA  ACTCAGGTAG  AACACACCTG  TCTTTGTCTT                      1773

GCTGTTTTCA  CTCAGCCCTT  TTAACATTTT  CCCCTAAGCC  CATATGTCTA  AGGAAAGGAT                      1833

GCTATTTGGT  AATGAGGAAC  TGTTATTTGT  ATGTGAATTA  AAGTGCTCTT  ATTTTAAAAA                      1893

A                                                                                            1894
```

( 2 ) INFORMATION FOR SEQ ID NO: 2:

( i ) SEQUENCE CHARACTERISTICS:
    ( A ) LENGTH: 9 amino acid residues
    ( B ) TYPE: amino acid
    ( D ) TOPOLOGY: linear ( x i ) SEQUENCE DESCRIPTION: SEQ ID NO: 2:

Tyr Met Asn Gly Thr Met Ser Gln Val
                  5

( 2 ) INFORMATION FOR SEQ ID NO: 3:

( i ) SEQUENCE CHARACTERISTICS:
        ( A ) LENGTH: 10 amino acid residues
        ( B ) TYPE: amino acid
        ( D ) TOPOLOGY: linear ( x i ) SEQUENCE DESCRIPTION: SEQ ID NO: 3:

Met Leu Leu Ala Val Leu Tyr Cys Leu Leu
                  5                        1 0

( 2 ) INFORMATION FOR SEQ ID NO: 4:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 4:

Met Leu Leu Ala Val Leu Tyr Cys Leu
                  5

( 2 ) INFORMATION FOR SEQ ID NO: 5:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 5:

Leu Leu Ala Val Leu Tyr Cys Leu Leu
                  5

( 2 ) INFORMATION FOR SEQ ID NO: 6:

( i ) SEQUENCE CHARACTERISTICS:
        ( A ) LENGTH: 13 amino acid residues
        ( B ) TYPE: amino acid
        ( D ) TOPOLOGY: linear ( x i ) SEQUENCE DESCRIPTION: SEQ ID NO: 6:

Ser Glu Ile Trp Arg Asp Ile Asp Phe Ala His Glu Ala
                  5                        1 0

( 2 ) INFORMATION FOR SEQ ID NO: 7:

( i ) SEQUENCE CHARACTERISTICS:
        ( A ) LENGTH: 10 amino acid residues
        ( B ) TYPE: amino acid
        ( D ) TOPOLOGY: linear ( x i ) SEQUENCE DESCRIPTION: SEQ ID NO: 7:

Ser Glu Ile Trp Arg Asp Ile Asp Phe Ala
                  5                        1 0

( 2 ) INFORMATION FOR SEQ ID NO: 8:

( i ) SEQUENCE CHARACTERISTICS:

(A) LENGTH: 9 amino acid residues
(B) TYPE: amino acid
(D) TOPOLOGY: linear (xi) SEQUENCE DESCRIPTION: SEQ ID NO: 8:

Ser Glu Ile Trp Arg Asp Ile Asp Phe
            5

(2) INFORMATION FOR SEQ ID NO: 9:

(i) SEQUENCE CHARACTERISTICS:
(A) LENGTH: 9 amino acid residues
(B) TYPE: amino acid
(D) TOPOLOGY: linear (xi) SEQUENCE DESCRIPTION: SEQ ID NO: 9:

Glu Ile Trp Arg Asp Ile Asp Phe Ala
            5

(2) INFORMATION FOR SEQ ID NO: 10:

(i) SEQUENCE CHARACTERISTICS:
(A) LENGTH: 10 amino acid residues
(B) TYPE: amino acid
(D) TOPOLOGY: linear (xi) SEQUENCE DESCRIPTION: SEQ ID NO: 10:

Glu Glu Asn Leu Leu Asp Phe Val Arg Phe
            5                        10

ISOLATED, TYROSINASE DERIVED PEPTIDES AND USES THEREOF

This application is a divisional of Ser. No. 08/233,305, filed Apr. 26, 1994, now U.S. Pat. No. 5,519,117, which is a continuation-in-part of Ser. No. 08/203,054 filed on Feb. 28, 1994, now U.S. Pat. No. 5,530,096, which is a continuation-in-part of application Ser. No. 08/081,673, filed Jun. 23, 1993, now U.S. Pat. No. 5,487,974, which is a continuation in part of U.S. patent application Ser. Number 054,714, filed Apr. 28, 1993 which is a continuation-in-part of U.S. patent application Ser. No. 994,928, filed Dec. 22, 1992, now abandoned.

FIELD OF THE INVENTION

This invention relates to isolated peptides, derived from tyrosinase which are presented by HLA-A2 and HLA-B44 molecules and uses thereof. In addition, it relates to the ability to identify those individuals diagnosed with conditions characterized by cellular abnormalities whose abnormal cells present complexes of these peptides and HLA-A2 and HLA-B44, the presented peptides, and the ramifications thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J.P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. patent application Ser. No. 938,334, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBO J 7: 2715 (1988)). An early report of CDNA for the human enzyme is found in Kwon, U.S. Pat. No. 4,898,814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application Ser. No. 08/081,673, filed Jun. 23, 1993 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules. These are described in Ser. No. 08/203,054, filed Feb. 28, 1994 and incorporated by reference.

It has now been found that additional peptides derived from tyrosinase are tumor rejection antigens in that they are presented by MHC molecule HLA-B44, and are lysed by cytolytic T cells.

BRIEF DESCRIPTION OF THE FIGURES

FIG. 1A shows lysis of cell line LB24-MEL, by CTL 210/9;

FIG. 1A' shows lysis of cell lines LB24-MEL, by CTL IVSB;

FIG. 1 shows lysis of cell lines SK29-MEL, by CTL 210/9;

FIG. 1B' shows lysis of cell line SK29-MEL, by CTL IVSB;

FIG. 1C shows lysis of cell line LB4.MEL, by CTL 210/9;

FIG. 1C' shows lysis of cell line LB4.MEL, by CTL IVSB;

FIG. 1D shows lysis of cell line SK23.MEL, by CTL 210/9;

FIG. 1D' shows lysis of cell line SK23.MEL, by CTL IVSB;

FIG. 1E shows lysis of cell line LE516.MEL, by CTL 210/9;

FIG. 1E' shows lysis of cell line LE516.MEL, by CTL IVSB;

FIG. 1F' shows lysis of cell line SK29-MEL.1.22 which has lost HLA-A2 expression, by CTL IVSB;

FIG. 1G shows lack of lysis of MZ2-MEL, by CTL 210/9;

FIG. 1G' shows lack of lysis of MZ2-MEL, by CTL IVSB;

FIG. 1H shows lysis of the loss variant in FIGS. 1F and 1F' after transfection with a gene for HLA-A2, by CTL 210/9;

FIG. 1H' shows lysis of the loss variant in FIGS. 1F and 1F' after transfection with a gene for HLA-A2, by CTL IVSB;

FIG. 1I shows lysis of the loss variant in FIGS. 1F and 1F' after transfection with a gene for HLA-A2, by CTL 210/9;

FIG. 1I' shows lysis of the loss variant in FIGS. 1F and 1F' after transfections with a gene for HLA-A2, by CTL IVSB.

FIG. 2 presents studies of TNF release of CTL IVSB.

FIG. 6 shows the results obtained when TNF release assays were carried out on various cells, including those which present HLA-B44 on their surface.

FIG. 7 shows, collectively, a series of chromium release assays using peptides described in this application on three different cell lines.

In FIG. 7, the symbol "○" is used for cell line T2, "■" for MZ2-MEL not presenting HLA-A2, and "●" for MZ2-MEL which has been transfected to present HLA-A2. Example 12 elaborates on these tests.

In FIG. 8A, the cell line ("Rosi EBV") was preincubated with monoclonal antibody W6/32, whereas in FIG. 8B, there was no preincubation.

DETAILED DESCRIPTION OF PREFERRED EMBODIMENTS

Example 1

Melanoma cell lines SK 29-MEL (also referred to in the literature as SK MEL-29) and LB24-MEL, which have been available to researchers for many years, were used in the following experiments.

Samples containing mononuclear blood cells were taken from patients SK29 (AV) and LB24 (these patients were also the source of SK 29-MEL and LB24-MEL, respectively). The melanoma cell lines were contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% of CO$_2$ atmosphere.

Plates were centrifuged again, and 100 ul aliquots of supernatant were collected and counted. Percentage of $^{51}$Cr release was calculated as follows:

$$\% \ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-transformed B cells (EBV-B cells) were used, the only change was the replacement of DMEM medium by Hank's medium, supplemented with 5% FCS.

These experiments led to isolation of CTL clone "IVSB" from patient SK29 (AV) and CTL clone 210/9 from patient LB24.

Figure 1F:
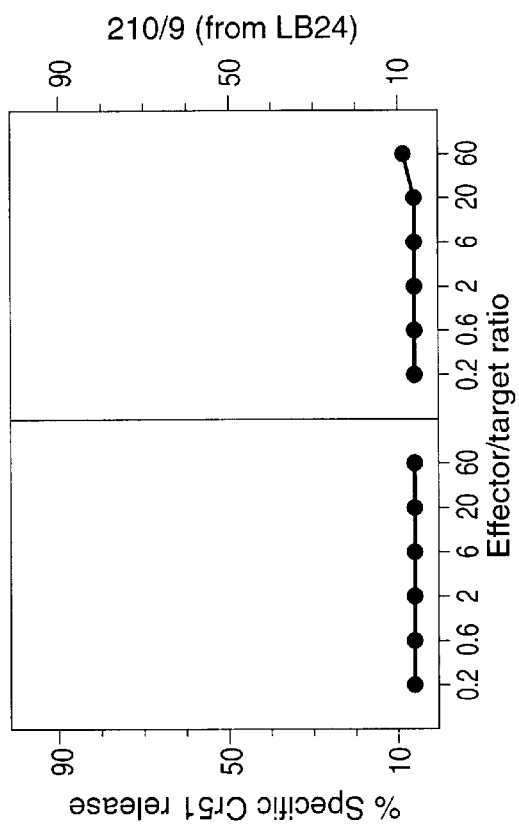
FIG. 1F shows lysis of cell line SK29-MEL.1.22 which has lost HLA-12 expression, by CTL 210/9.
Figures 1, 1F:
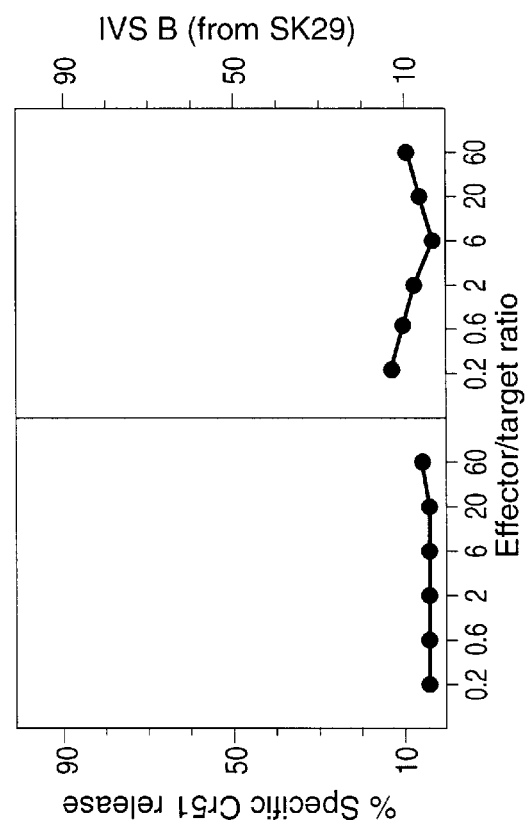
FIG. 1 describes, collectively, cell lysis studies. In particular.

FIG. 1 presents the results of these assays, in panels A, B, G and I. Specifically, it will be seen that both CTLs lysed both melanoma cell lines, and that there was no lysis of the K562 and EBV-B cell lines.

Example 2

The CTLs described were tested against other melanoma cell lines to determine whether their target was shared by other melanoma cell lines. Lysis as described in Example 1 was studied for lines LB4.MEL, SK23.MEL (also known as SK MEL-23), and LE516.MEL. FIG. 1, panels C, D and E shows that the clones did lyse these lines.

The tested lines are known to be of type HLA-A2, and the results suggested that the CTLs are specific for a complex of peptide and HLA-A2. This suggestion was verified by testing a variant of SK 29-MEL which has lost HLA-A2 expression. FIG. 1, panel F shows these results. Neither clone lysed the HLA-loss variant. When the variant was transfected with the HLA-A2 gene of SK29-MEL, however, and retested, lysis was observed. Thus, it can be concluded that the presenting molecule is HLA-A2.

Example 3

Once the presenting HLA molecule was identified, studies were carried out to identify the molecule, referred to hereafter as the "tumor rejection antigen precursor" or "TRAP" molecule which was the source of the presented peptide.

To do this, total RNA was isolated from cell line SK29-MEL.1, which is a subclone of SK29-MEL. The RNA was isolated using an oligo-dT binding kit, following well recognized techniques. Once the total RNA was secured, it was transcribed into cDNA, again using standard methodologies. The CDNA was then ligated to EcoRI adaptors and cloned into the EcoRI site of plasmid pcDNA-I/Amp, in accordance with manufacturer's instructions. The recombinant plasmids were then electroporated into JM101 *E. coli (electroporation conditions:* 1 pulse at 25 μfarads, 2500 V).

The transfected bacteria were selected with ampicillin (50 μg/ml), and then divided into 700 pools of 200 clones each. Each pool represented about 100 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

Example 4

The amplified plasmids were then transfected into eukaryotic cells. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, 100 ng of plasmid pcDNA-I/Amp-A2 and 100 ng of DNA of a pool of the cDNA library described supra. Plasmid pcDNA-I/Amp-A2 contains the HLA-A2 gene from SK29-MEL. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 2000 cells of either of the described CTL clones were added, in 100 μl of Iscove's medium containing 10% pooled human serum. When clone 210/9 was used, the medium was supplemented with 25 U/ml of IL-2. Supernatant was removed after 24 hours, and TNF content was determined in an assay on WEHI cells, as described by Traversari et al., Immunogenetics 35: 145–152 (1992), the disclosure of which is incorporated by reference.

Figure 3:
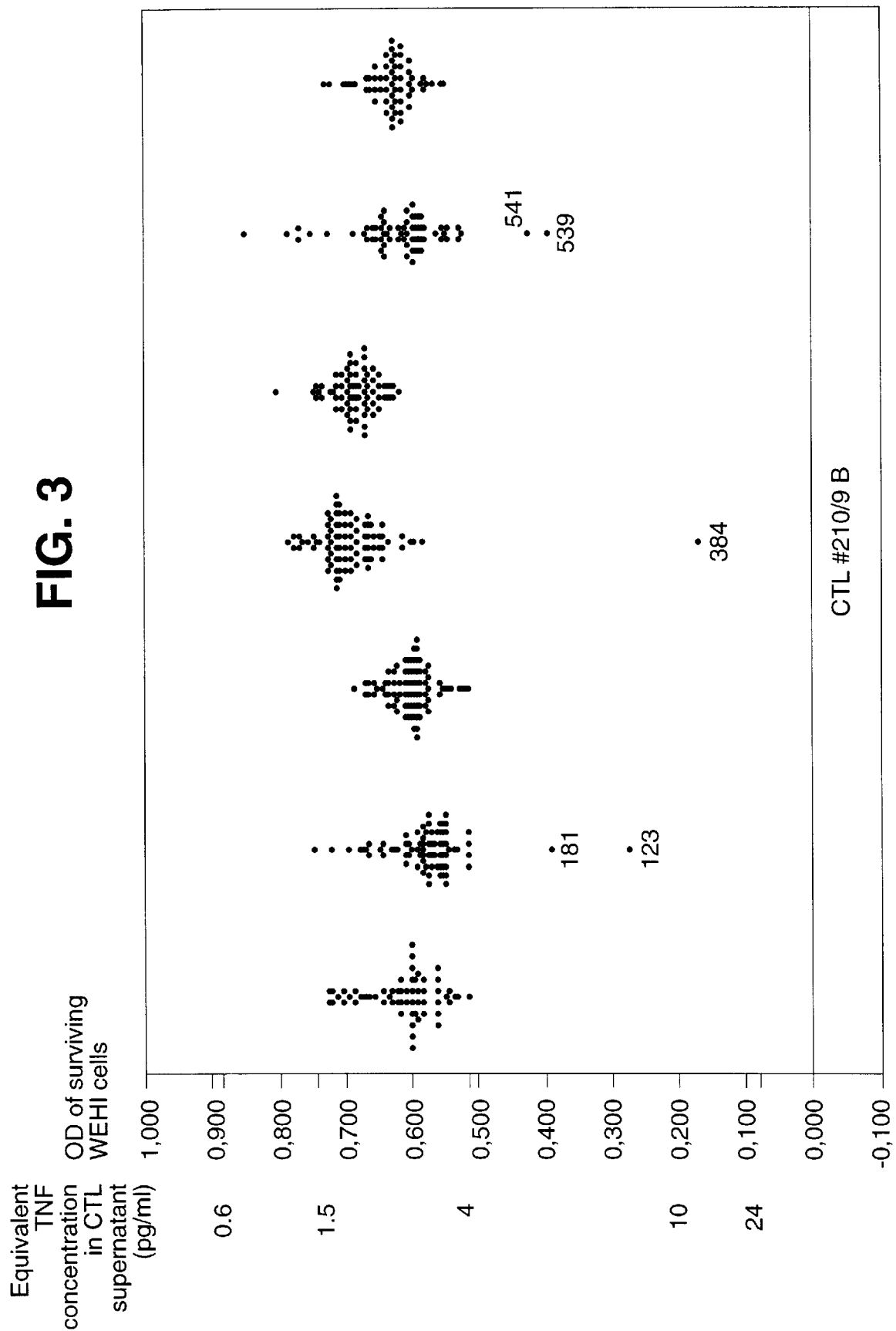
FIG. 3 depicts studies of TNF release of CTL 210/9.

Of 700 wells tested with IVSB, 696 showed between 0.6 and 4 pg of TNF per ml. The remaining four wells contained between 10 and 20 pg/ml of TNF. Homologous wells tested with CTL 210/9 showed similar, clearly higher values. FIGS. 2 and 3 present these data.

Example 5

Three of the four pools identified as high producers (numbers "123", "181" and "384") were selected for further experiments. Specifically, the bacteria were cloned, and 570 bacteria were tested from each pool. Plasmid DNA was extracted therefrom, transfected into a new sample of COS cells in the same manner as described supra, and the cells were again tested for stimulation of CTL 210/9 and CTL IVSB. A positive clone was found in pool 123 ("p123.B2"), and one was found in pool 384 ("p384.C6"). Convincing evidence that the transfected cells were recognized by CTLs was obtained by carrying out a comparative test of COS cells transfected with cDNA and the HLA-A2 gene, and COS cells transfected only with HLA-A2. TNF release in CTL supernatant was measured by testing it on WEHI cells. The optical density of the surviving WEHI cells was measured using MTT. Results are presented in Table 1:

TABLE 1

|  | cDNA (123.B2) + HLA-A2 DNA | no cDNA + HLA-A2 |
|---|---|---|
| Run 1 | 0.087 | 0.502 |
| Run 2 | 0.108 | 0.562 |

The values for WEHI OD's correspond to 24 pg/ml of TNF for CDNA and HLA-A2, versus 2.3 pg/ml for the control.

The plasmids from the positive clones were removed, and sequenced following art known techniques. A sequence search revealed that the plasmid insert was nearly identical to the cDNA for human tyrosinase, as described by Bouchard et al., J. Exp. Med. 169: 2029 (1989), the disclosure of which is incorporated by reference. Thus, a normally occurring molecule (i.e., tyrosinase), may act as a tumor rejection antigen precursor and be processed to form a peptide tumor rejection antigen which is presented on the surface of a cell, in combination with HLA-A2, thereby stimulating lysis by CTL clones. The nucleic sequence of the identified molecule is presented as SEQ ID NO: 1.

Example 6

Prior work reported by Chomez et al., Immunogenetics 35: 241 (1992) has shown that small gene fragments which contain a sequence coding for an antigenic peptide resulted in expression of that peptide. This work, which is incorporated by reference in its entirety, suggested the cloning of small portions of the human tyrosinase CDNA described supra and in SEQ ID NO: 1. Using the methodologies described in examples 1–5, various fragments of the CDNA were cotransfected with a gene for HLA-A2 in COS-7 cells, and TNF release assays were performed. These experiments led to identification of an approximately 400 base pair fragment which, when used in cotransfection experiments, provoked TNF release from cytolytic T cell clone CTL IVSB discussed supra, shown to be specific for HLA-A2 presenting cells. The approximately 400 base fragment used corresponded to bases 711 to 1152 of SEQ ID NO: 1. The amino acid sequence for which the fragment codes was deduced, and this sequence was then compared to the information provided by Hunt et al., Science 255: 1261 (1992), and Falk et al., Nature 351: 290 (1991), the disclosures of which are both incorporated by reference in their entirety. These references discuss consensus sequences for HLA-A2 presented peptides. Specifically, Hunt discusses nonapeptides, where either Leu or Ile is always found at the second position, Leu being the "dominant residue". The ninth residue is described as always being a residue with an aliphatic hydrocarbon side chain. Val is the dominant residue at this position. Hunt discusses a strong signal for Leu and an intermediate signal for Met at the second position, one of Val, Leu, Ile or Thr at position 6, and Val or Leu at position 9, with Val being particularly strong. On the basis of the comparison, nonapeptides were synthesized and then tested to see if they could sensitize HLA-A2 presenting cells. To do so, tyrosinase loss variant cell lines SK29-MEL 1.218 and T202LB were used. Varying concentrations of the tested peptides were added to the cell lines, together with either of cytolytic T cell clone CTL IVSB or cytolytic T cell clone CTL 210/9. Prior work, described supra, had established that the former clone lysed tyrosinase expressing cells which present HLA-A2, and that the latter did not.

The tyrosinase loss variants were incubated for one hour in a solution containing $^{51}$Cr, at 37° C., either with or without anti HLA-A2 antibody MA2.1, which was used to stabilize empty HLA-A2 molecules. In the tests, cells were washed four times, and then incubated with varying dilutions of the peptides, from 100 μM down to 0.01 μM. After 30 minutes, effector cells were added at an E/T ratio of 40/1 and four hours later, 1oox of supernatant were collected and radioactivity counted.

Figure 4A:
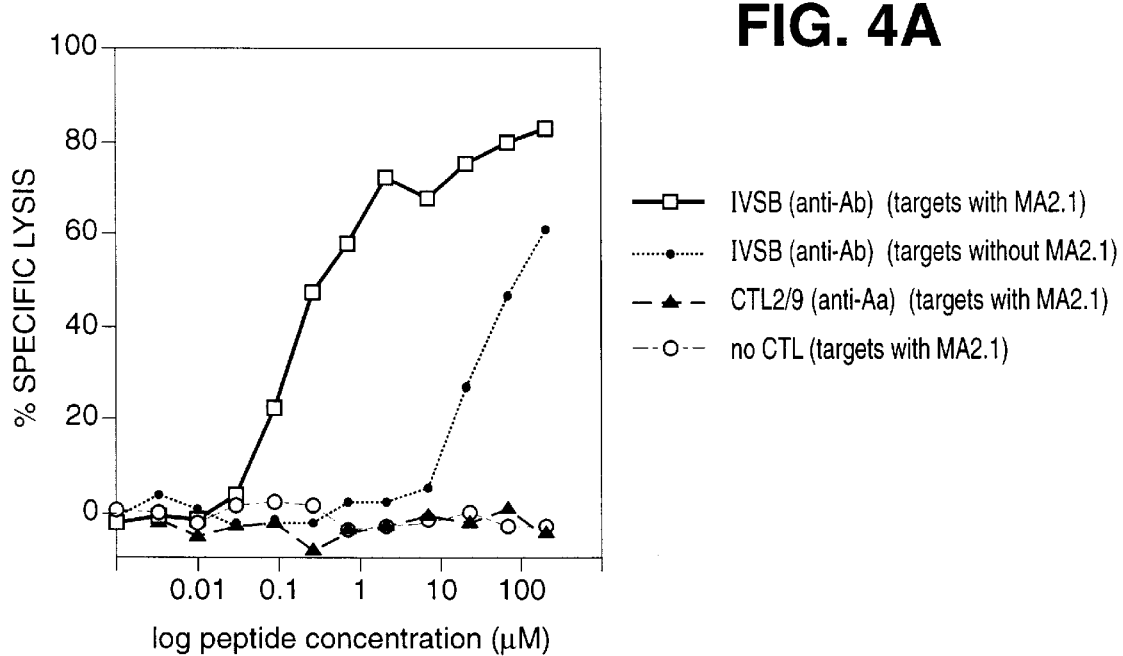
FIGS. 4A and 4B; the recognition of the peptide SEQ ID NO:2 by cytolytic T cell clone CTL-IVSB but not cytolytic T cell clone CTL 2/9.
Figure 4B:
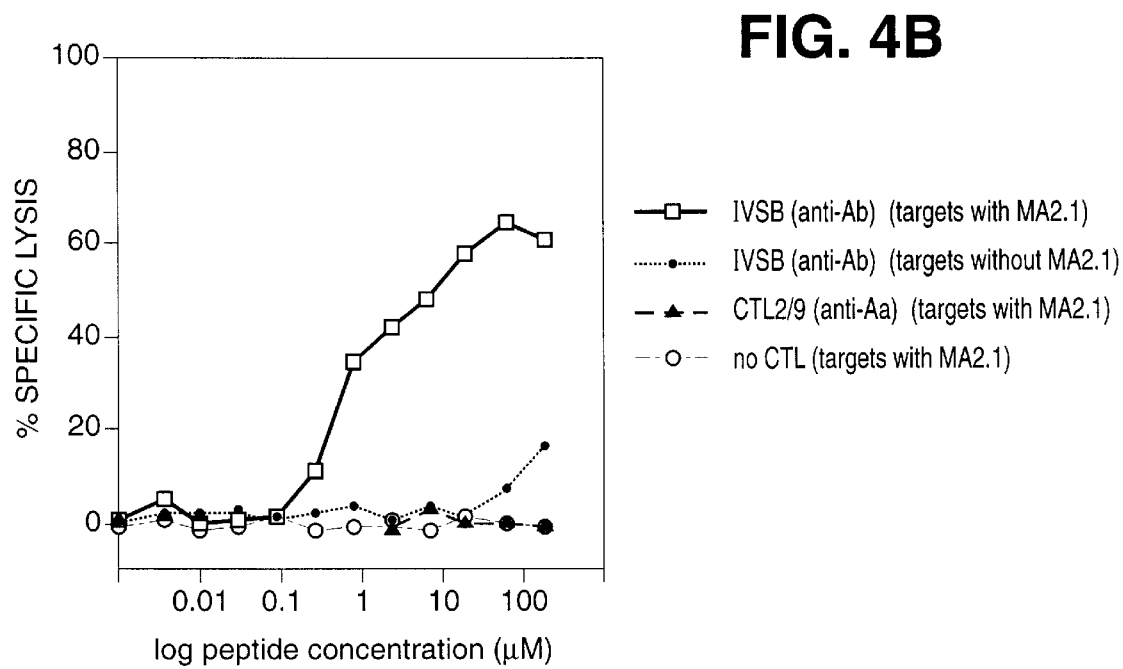
Figure 5:
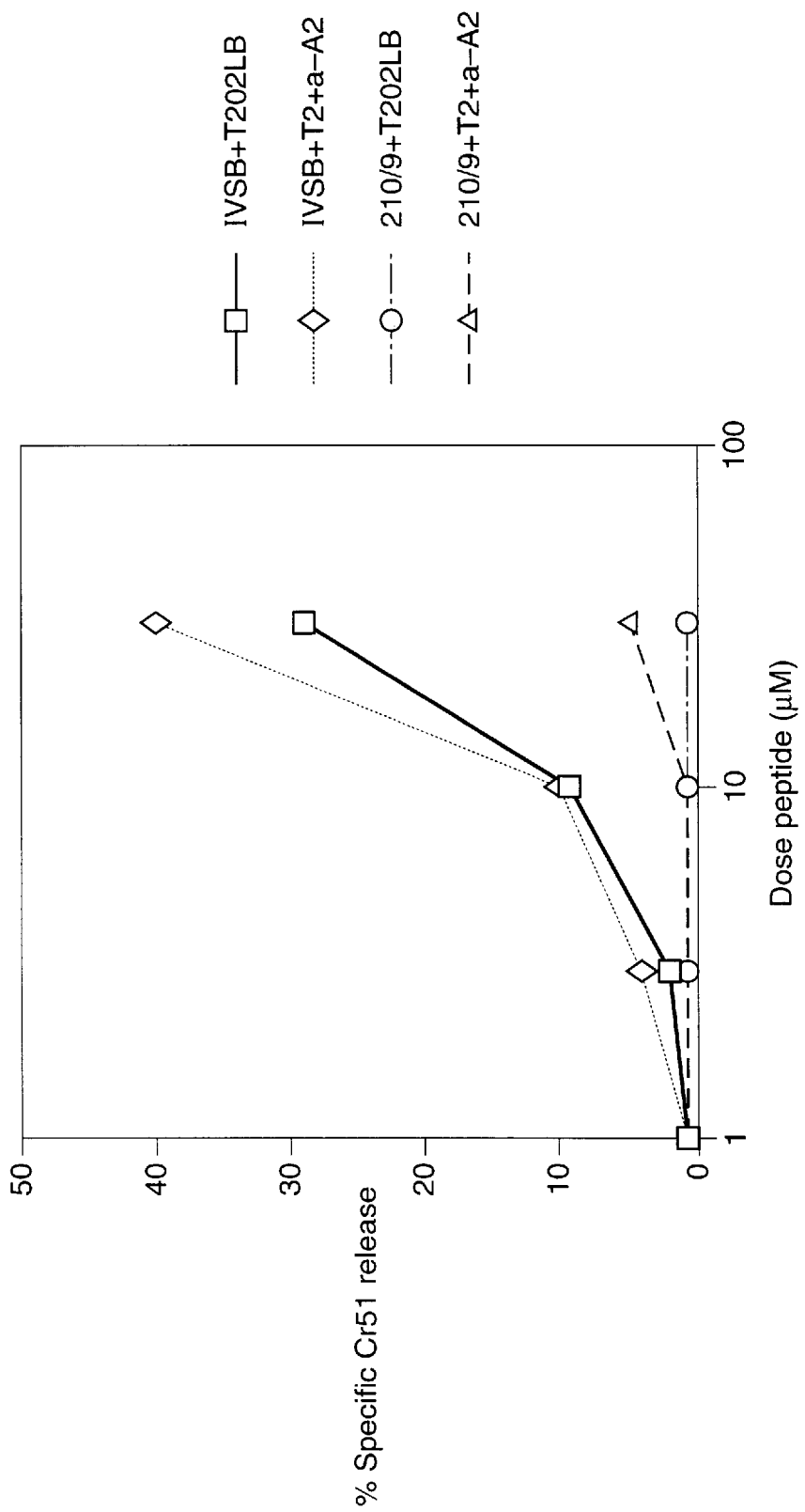
FIG. 5 shows that the peptide YMNGTMSQV is not recognized by cytolytic T cell clone CTL 210/9.

FIG. 4 shows the results obtained with nonapeptide

Tyr Met Asn Gly Thr Met Ser Gln Val. (SEQ ID NO: 2).

This peptide, referred to hereafter as SEQ ID NO: 2, corresponds to residues 1129–1155 of the cDNA sequence for tyrosinase presented in SEQ ID NO: 1. Complexes of HLA-A2 and this peptide are recognized by CTL clone IVSB.

In a parallel experiment, it was shown that CTL clone CTL 210/9, derived from patient LB24, did not recognize the complexes of HLA-A2 and the peptide of SEQ ID NO: 2, although it did recognize complexes of HLA-A2 and a tyrosinase derived peptide. Thus, tyrosinase is processed to at least one additional peptide which, when presented by HLA-A2 molecules, is recognized by CTL clones.

Example 7

In a follow-up experiment, a second gene fragment which did not encode the peptide of SEQ ID NO: 2 was used. This fragment began at base 1 and ended at base 1101 of SEQ ID NO: 1 (i.e. the EcoRI-SphI fragment). Cytolytic T cell clone CTL 210/9, discussed supra, was tested against COS-7 cells transfected with this fragment in the manner described supra. CTL IVSB was also tested. These results showed that CTL 210/9 recognized an antigen on the surface of HLA-A2 expressing cells transfected with this fragment, but CTL IVSB did not. Thus, a second tumor rejection antigen peptide is derived from tyrosinase.

Example 8

In order to further define the tumor rejection antigen recognized by CTL 210/9, the following experiments were carried out.

A second fragment, corresponding to bases 451–1158 of SEQ ID NO: 1 was transfected into COS cells together with a gene for HLA-A2, and TNF release assays were carried out. This sequence provoked TNF release from clone SK29-CTL IVSB (20 pg/ml), but not from LB24-CTL 210/9 (3.8 pg/ml). These results confirmed that the two CTL clones recognize different peptides, and that the peptide recognized by CTL 210/9 must be encoded by region 1–451.

Example 9

The tyrosinase derived peptide coded for by cDNA fragment 1–451 was analyzed for consensus sequences known to bind HLA-A2. The peptides corresponding to these consensus sequences were synthesized, and tested for their ability to sensitize HLA-A2 presenting cells. To do so, two tyrosinase negative melanoma cell lines were used (i.e., NA8-MEL, and MZ2-MEL 2.2 transfected with HLA-A2), and cell line T2, as described by Salter et al, Immunogenetics 21: 235–246 (1985)).

The cells were incubated with $^{51}$Cr, and monoclonal antibody MA2.1, which is specific for HLA-A2 for 50 minutes at 37° C., followed by washing (see Bodmer et al., Nature 342: 443–446 (1989), the disclosure of which is incorporated by reference in its entirety). Target cells were incubated with various concentrations of the peptides, and with either of LB 24-CTL clones 210/5 or 210/9. The percent of chromium release was measured after four hours of incubation.

The peptide Met Leu Leu Ala Val Leu Tyr Cys Leu Leu (SEQ ID NO: 3) was found to be active.

In further experiments summarized here, CTL-IVSB previously shown to recognize SEQ ID NO:2, did not recognize the peptide of SEQ ID NO: 3.

The results are summarized in Tables 2–4 which follow:

TABLE 2

| | Peptide | |
|---|---|---|
| | SEQ ID NO: 2 | SEQ ID NO: 3 |
| CTL-IVSB | + | − |
| CTL-210/5 | − | + |
| CTL-210/9 | − | + |

TABLE 3

Lysis of MZ2-2.2.2 sensitized with tyrosinase peptides by CTL 210/5, CTL 210/9, and CTL IVSB

| Effectors | Peptides | Dose | MZ2.22.A2 + anti-A2* |
|---|---|---|---|
| CTL 210/5 (44:1) | SEQ ID NO: 3 | 10 μM | 13 |
| | | 1 | 17 |
| | SEQ ID NO: 2 | 30 μM | 16 |
| | | 10 | 1 |
| | | 3 | 1 |
| | | 10 μm | 13 |
| | | 3 | 17 |
| CTL 210/9 (20:1) | SEQ ID NO: 3 | 1 | 15 |
| | SEQ ID NO: 2 | 30 M | 1 |
| | | 10 | 1 |
| | | 3 | 1 |
| | | 10 μM | 1 |
| CTL IVSB (40:1) | SEQ ID NO: 3 | 3 | 1 |
| | | 1 | 1 |
| | SEQ ID NO: 2 | 30 μM | 63 |
| | | 10 | 63 |
| | | 3 | 62 |

*Target cells were incubated with $^{51}$Cr and mono-Ab MA2.1 (anti-HLA-A2) for 50 minutes, then washed three times. They were incubated with various concentration of peptides for 30 min. CTL cells were added at the indicated (E:T) ratio. The % specific $^{51}$Cr release was measured after 4 h incubation.

TABLE 4

Test of tyrosinase peptides recognized by LB24-CTL 210/5 and 210/9 or SK29-CTL IVSB

| | | | (% Cr51 specific release) | | |
|---|---|---|---|---|---|
| Effectors | Peptides | Dose | NAS-MEL* | MZ2-2.2; A2 | T2 |
| LB24-CTL 210/5 (41:1) | MLLAVLYCLL (LAUS 17-5) | 10 μM | 30 | 31 | 36 |
| | | 3 | 23 | 27 | 35 |
| | | 1 | 17 | 20 | 26 |
| | | 300 nM | 8 | 17 | 18 |
| | | 100 | 2 | 8 | 5 |
| | | 30 | 3 | 5 | 2 |
| | | 0 | 0 | 0 | 0 |
| LB24-CTL | MLLAVLYCLL | 10 μM | 14 | 19 | 21 |

TABLE 4-continued

Test of tyrosinase peptides recognized by
LB24-CTL 210/5 and 210/9 or SK29-CTL IVSB

| Effectors | Peptides | Dose | (% Cr51 specific release) | | |
|---|---|---|---|---|---|
| | | | NAS-MEL* | MZ2-2.2; A2 | T2 |
| 210/9 (28:1) | (LAUS 17-5) | 3 | 13 | 17 | 20 |
| | | 1 | 9 | 14 | 13 |
| | | 300 nM | 3 | 9 | 5 |
| | | 100 | 1 | 1 | 1 |
| | | 30 | 0 | 1 | 0 |
| | | 0 | 0 | 1 | 0 |
| SK29-CTL IVSB (42:1) | YMNGTMSOV (MAINZ) | 10 μM | 46 | 48 | 59 |
| | | 3 | 38 | 44 | 52 |
| | | 1 | 27 | 40 | 46 |
| | | 300 nM | 14 | 22 | 34 |
| | | 100 | 3 | 13 | 21 |
| | | 30 | 1 | 9 | 10 |
| | | 10 | 1 | 3 | 3 |
| | | 3 | 0 | 3 | 4 |
| | | 1 | 0 | 1 | 0 |
| | | 0 | 0 | 4 | 0 |
| spt. rel. | | | 339 | 259 | 198 |
| max-spt | | | 2694 | 1893 | 1208 |
| % | | | 11 | 13 | 14 |

Example 10

Additional experiments were carried out using CTL clone 22/31. This clone had previously been shown to lyse subline MZ2-MEL.43 from autologous melanoma cell line MZ2-MEL, but did not lyse other sublines, such as MZ2-MEL 3.0 and MZ2-MEL 61.2, nor did it lyse autologous EBV transformed B cells, or killer cell line K562 (see Van den Eynde et al., Int. J. Cancer 44: 634–640 (1989)). The antigen presented by MZ2-MEL.43 is referred to as antigen C.

In prior work including that reported in the parent of this application, it was found that the tyrosinase gene encodes an antigen recognized by autologous CTLs on most HLA-A2 expressing melanomas. Expression of this gene in sublines of cell line MZ2-MEL was tested by PCR amplification. Clone MZ2-MEL.43 was found to be positive, whereas other MZ2-MEL clones, such as MZ2-MEL.3.0 were negative. Correlation of expression of the tyrosinase gene, and antigen MZ2-C, suggested that MZ2-C might be a tumor rejection antigen derived from tyrosinase, and presented by an HLA molecule expressed by MZ2-MEL. This cell line does not express HLA-A2, which would indicate that if a tyrosinase derived peptide were presented as a TRA, a second HLA molecule was implicated.

Studies were carried out to identify which HLA molecule presented antigen C to CTL 22/31. To determine this, cDNA clones of the HLA molecules known to be on the cell surface, i.e., HLA-A29, HLA-B37, HLA-B 44.02, and HLA-C clone 10, were isolated from an MZ2-MEL.43 cDNA library, and then cloned into expression vector pcDNAI/Amp. Recipient COS 7 cells were then transfected with one of these constructs or a construct containing HLA-A1, plus CDNA coding for tyrosinase (SEQ ID NO: 1). The contransfection followed the method set forth above. One day later CTL 22/31 was added, and 24 hours later, TNF release was measured by testing cytotoxicity on WEHI-164-13, following Traversari et al, supra. FIG. 6 shows that TNF was released by CTL 22/31 only in the presence of cells transfected with both HLA-B44 and tyrosinase. The conclusion to be drawn from this is that HLA-B44 presents a tyrosinase derived tumor rejection antigen.

Example 11

The experiments described supra showed, inter alia, that the decamer of SEQ ID NO:3 effectively induced lysis of HLA-A2 presenting cells. It is fairly well accepted that MHC molecules present nonapeptides. To that end, experiments were carried out wherein two nonamers were tested, which were based upon the decapeptide which did give positive results. Specifically, either the first or tenth amino acid was omitted to create two peptides, i.e.:

Met Leu Leu Ala Val Leu Tyr Cys Leu
(SEQ ID NO: 4)

Leu Leu Ala Val Leu Tyr Cys Leu Leu
(SEQ ID NO: 5).

These peptides were tested in the same way the decapeptide was tested, as set forth in the prior examples at concentrations ranging from 10 μM to 1 nM. Three presenting cells were used. As summarized in Table 5, which follows, "T2" is a mutant human cell line, "CEMX721.174T2" as described by Salter, Immunogenetics 21: 235(1985). This line presents HLA-A2. "G2.2" is a variant of the cell line MZ2-MEL. The variant has been transfected with a gene coding for HLA-A2. The abbreviation "G2.2.5" stands for a variant which does not express HLA-A2. All cells were incubated with monoclonal antibody MA2.1 prior to contact with the cytolytic T cell clone. This procedure stabilizes so-called "empty" MHC molecules, although the mechanism by which this occurs is not well understood and effector CTLs 210/5 and 210/9 were both used. The results are set forth in Table 5, which follows. They show that at a concentration of 10 μM, the nonamer of SEQ ID NO: 4 was twice as effective when used with CTL clone 210/5, and four times as effective with clone 210/9 whereas the nonamer of SEQ ID NO: 5 was ineffective at inducing lysis.

Example 12

In further experiments, chromium release assays were carried out using the peptides of SEQ ID NOS: 4 and 5, as well as SEQ ID NO: 2. The target cells were allogeneic melanoma cells, i.e., MZ2-MEL, previously transfected with HLA-A2, and cell line T2, which presents HLA-A2, but has an antigen processing defect which results in an increased capacity to present exogenous peptides (Cerundolo et al., Nature 345: 449 (1990)). All cells were pretreated with monoclonal antibody MA2.1 for fifty minutes. The cells were incubated with the peptide of choice, for 30 minutes, at various concentrations. Then, one of CTL clones 210/9 and ISVB was added in an effector: target ratio of 60. Chromium release was measured after four hours, in the manner described supra.

Figure 7C:
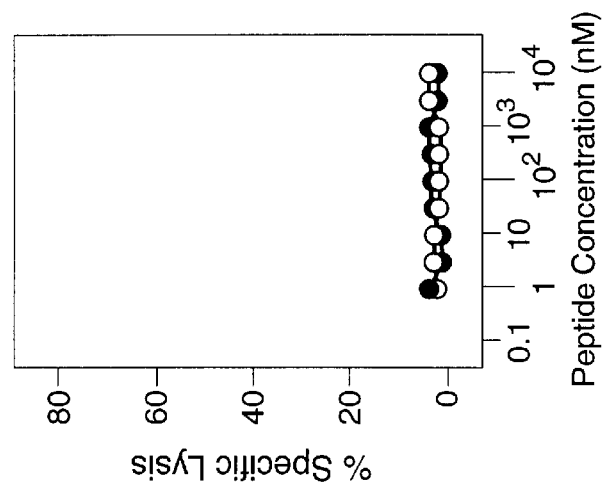
FIGS. 7C and 7F set forth results obtained using SEQ ID NO: 2.
Figure 7B:
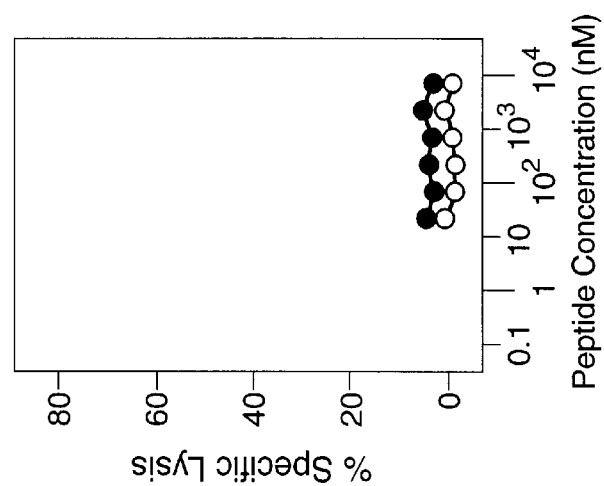
FIGS. 7B and 7E show results where the peptide of SEQ ID NO: 5 was used.
Figure 7A:
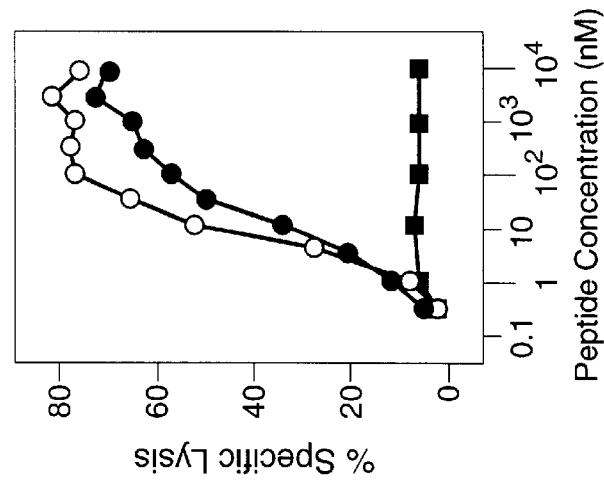
FIGS. 7A and 7D present experiments where the peptide of SEQ ID NO: 4 was used.
Figure 7D:
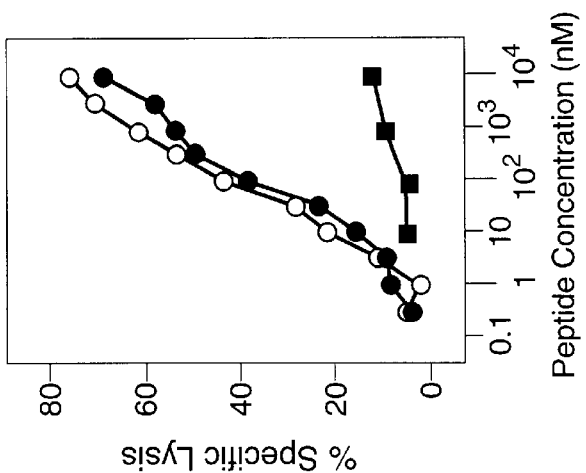
Figure 7E:
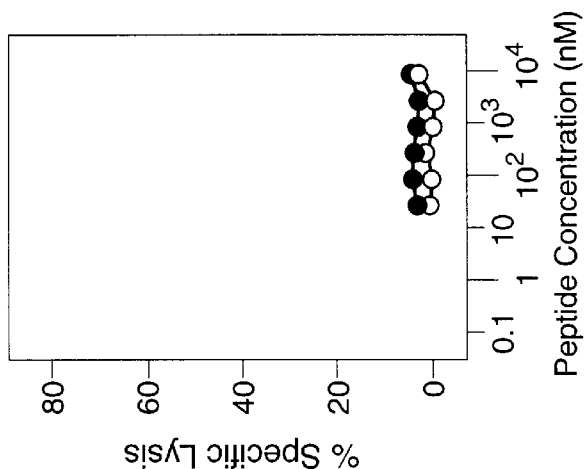
Figure 7F:
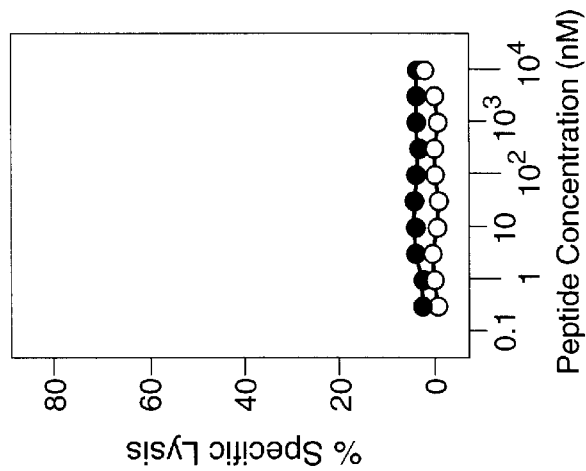

The results are presented in FIG. 7, i.e., FIGS. 7A–7C. The peptide of SEQ ID NO: 4 sensitized cells to CTL 210/9, while SEQ ID NO: 5 did not. SEQ ID NO: 2 sensitized cells to CTL IVSB, as already noted in previous examples.

TABLE 5

| Effecteur | Peptide | Dose | T2 + s-A2 | G2.2 + s-A2 | G2.2.5 + s-A2 | | Effectuer | Peptide | Dose | T2 + s-A2 | G 2.2 + s-A2 | G2.2.5 + s-A2 |
|---|---|---|---|---|---|---|---|---|---|---|---|---|
| DAGI 210/5 50:1 | MLLAVLYCLL (LAUS 17-5) | 10 μM | | 32 | 3 | | SK29 IVS8 60:1 | MMLAVLYCLL (LAUS 17-5) | 10 μM | 3 | 3 | 7 |
| | | 3 | 45 | 32 | 5 | | | | 3 | 0 | 2 | 7 |
| | | 1 | 39 | 26 | 3 | | | | 1 | 2 | 3 | 4 |
| | | 300 nM | 33 | 18 | 4 | | | | 300 nM | 3 | 1 | 6 |
| | | 100 | 24 | 8 | 5 | | | | 100 | 1 | 2 | 7 |
| | | 30 | 13 | 5 | 5 | | | | 30 | 1 | 4 | 7 |
| | | 10 | 6 | 5 | 5 | | | | 10 | 0 | 3 | 7 |
| | | 3 | 2 | 2 | 4 | | | | 3 | 2 | 4 | 7 |
| | | 1 | 2 | 1 | 3 | | | | 1 | 2 | 4 | 6 |
| | | 300 pg | 1 | 4 | 3 | | | | 300 pg | 1 | 4 | 7 |
| | MMLAVLYCL (LAUS 19-5) | 10 μM | 98 | 65 | 7 | | | MLLAVLYCL (LAUS 19-5) | 10 μM | 2 | 3 | 6 |
| | | 3 | 67 | 60 | 4 | | | | 3 | 1 | 4 | 6 |
| | | 1 | 95 | 66 | 5 | | | | 1 | 0 | 4 | 6 |
| | | 300 nM | 95 | 60 | 3 | | | | 300 nM | 1 | 3 | 7 |
| | | 100 | 91 | 56 | 3 | | | | 100 | 1 | 4 | 6 |
| | | 30 | 87 | 48 | 3 | | | | 30 | 0 | 4 | 6 |
| | | 10 | 82 | | 6 | | | | 10 | 0 | 4 | 6 |
| | | 3 | 78 | | 4 | | | | 3 | 1 | 4 | 6 |
| | | 1 | 78 | | 5 | | | | 1 | 1 | 3 | 8 |
| | | 300 pg | 78 | | 5 | | | | 300 pg | 0 | 3 | 6 |
| | LLAVLYCLL (Laus 19-10) | 10 μM | 0 | 1 | 3 | | | LLAVLYCLL (Laus 19-10) | 10 μM | 3 | 6 | 7 |
| | | 3 | 0 | 2 | 4 | | | | 3 | 0 | 3 | 7 |
| | | 1 | 3 | 3 | 3 | | | | 1 | 1 | 3 | 6 |
| | | 300 nM | 0 | 2 | 4 | | | | 300 nM | 2 | 3 | 6 |
| | | 100 | 1 | 2 | 4 | | | | 100 | 1 | 5 | 5 |
| | | 30 | 1 | 1 | 2 | | | | 30 | 1 | 4 | 10 |
| | YMNGTMSQV (MAIN2) | 10 μM | 4 | 3 | 4 | | | YMNGTMSQV (MAIN2) | 10 μM | 78 | 69 | 8 |
| | | 3 | 4 | 1 | 5 | | | | 3 | 73 | 60 | 4 |
| | | 1 | 2 | 2 | 4 | | | | 1 | 62 | 55 | 7 |
| | | 300 nM | 1 | 3 | 2 | | | | 300 nM | 56 | 51 | 6 |
| | | 100 | 0 | 1 | 6 | | | | 100 | 46 | 40 | 7 |
| | | 30 | 0 | 2 | 4 | | | | 30 | 30 | 25 | 7 |
| | | 10 | 0 | | 3 | | | | 10 | 23 | 18 | 8 |
| | | 3 | 3 | 3 | 3 | | | | 3 | 13 | 11 | 4 |
| | | 2 | 2 | | 5 | | | | 1 | 3 | 9 | 5 |
| | | | | | | | | | 300 pg | 7 | 7 | 8 |
| | 0 | 0 | 0 | 3 | 7 | | | | 100 | 4 | 7 | 7 |
| | | | | | | | | | 30 | 2 | 7 | 8 |
| DAG 210/3 60:1 | MLLAVLYCLL (LAUS 17-5) | 10 μM | 26 | 23 | 8 | | | | | | | |
| | | 3 | 20 | 23 | 6 | | | | 0 | 2 | 3 | 5 |
| | | 1 | 19 | 22 | 9 | | | | | | | |
| | | 300 nM | 13 | 16 | 7 | | spt. ref. | | | 184 | 441 | 195 |
| | | 100 | 10 | 9 | 6 | | max-spt % | | | 1033 | 2522 | 1686 |
| | | 30 | 5 | 6 | 7 | | | | | 15 | 15 | 10 |
| | | 10 | 3 | 4 | 6 | | | | | | | |
| | | 3 | 5 | 9 | 5 | | | | | | | |
| | | 1 | 7 | 3 | 6 | | | | | | | |
| | | 300 pg | 1 | 4 | 8 | | | | | | | |
| | | 100 | 1 | 3 | 8 | | | | | | | |
| | | 30 | 1 | 4 | 7 | | | | | | | |
| | MLLAVLYCL (LAUS 19-5) | 10 μM | 98 | 82 | 12 | | | | | | | |
| | | 3 | 92 | 75 | 10 | | | | | | | |
| | | 1 | 89 | 74 | 6 | | | | | | | |
| | | 300 nM | 95 | 67 | 6 | | | | | | | |
| | | 100 | 87 | 63 | 6 | | | | | | | |
| | | 30 | 93 | 53 | 5 | | | | | | | |
| | | 10 | 82 | 42 | 9 | | | | | | | |
| | | 3 | 87 | 34 | 3 | | | | | | | |
| | | 1 | 77 | 30 | 7 | | | | | | | |
| | | 300 pg | 70 | 25 | 7 | | | | | | | |
| | | 100 | 73 | 27 | 6 | | | | | | | |
| | | 30 | 41 | 22 | 6 | | | | | | | |
| | LLAVLYCLL (Laus 19-10) | 10 μM | 1 | 3 | 7 | | | | | | | |
| | | 3 | 1 | 3 | 8 | | | | | | | |
| | | 1 | 4 | 4 | 9 | | | | | | | |

Example 13

Work which followed up on the experiments set forth in example 10 was then carried out, in an effort to define the antigenic peptide presented by HLA-B44. To do so, cDNA sequences corresponding to fragments of the tyrosinase cDNA sequence were cotransfected, together with a gene coding for HLA-B44, into COS-7 cells. The protocol is essentially that described in example 6, supra. The cytolytic T cell clone 22/31, discussed supra, was used. TNF release was determined. Two fragments, i.e., base fragments 1–611, and 427–1134 induced TNF release. This suggested that the presented peptide was in the overlapping region. As a result of this observation, shorter fragments were tested. Fragments beginning at positions 385, 442, 514 and 574 were able to induce TNF release, while fragments starting at positions 579 and 585 were not. These observations, in turn, suggested the synthesis, following standard methodologies, of a 13 amino acid peptide beginning at position 574.

This peptide was then used in experiments to determine whether it induced lysis by CTL 22/31. Table 6, which follows, shows that the 13-mer rendered two EBV transfected cell lines which express HLA-B44 sensitive to lysis.

TABLE 6

10F94-tyros 13-mer sur EBV-I

| | 1<br>Effector | 2<br>Dose pept 13 A.A. | 3<br>Rosi-EBV | 4<br>MZ2-EBV |
|---|---|---|---|---|
| 1 | MZ2-CTL-22/31 | Ser Glu Ile Trp Arg Asp Ile Asp Phe Ala His Glu Ala | | |
| 2 | (SEQ ID NO: 6) | | | |
| 3 | 60:1 | 30 μM | 83 | 71 |
| 4 | | 10 | 85 | 72 |
| 5 | | 3 | 77 | 66 |
| 6 | | 1 | 79 | 63 |
| 7 | | 300 nM | 60 | 33 |
| 8 | | 100 | 44 | 17 |
| 9 | | 30 | 21 | 4 |
| 10 | | 10 | 9 | 5 |
| 11 | | 3 | 10 | 6 |
| 12 | | | | |
| 13 | | 0 | 10 | 6 |
| 14 | | | | |
| 15 | spt. rel. | | 393 | 472 |
| 16 | max. rel. | | 1698 | 1792 |
| 17 | % | | 23 | 26 |

As a follow up, even shorter peptides were tested. A decamer corresponding to nucleotide bases 574–604, i.e.

Ser Glu Ile Trp Arg Asp Ile Asp Phe Ala (SEQ ID NO: 7)

did provoke lysis, as did peptide:

Ser Glu Ile Trp Arg Asp Ile Asp Phe (SEQ ID NO: 8)

Figure 8A:
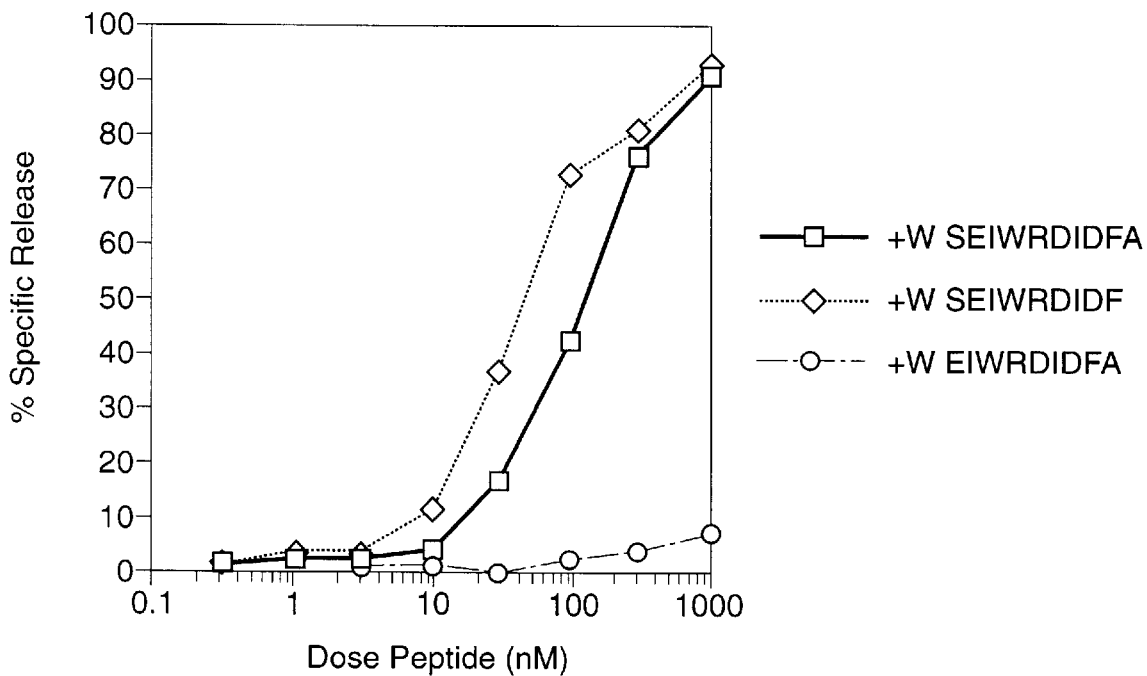
FIGS. 8A and 8B show work using a cell line which presents MHC molecule HLA-B44, and cytolytic T cell clone 22/31 ("CTL 22/31" hereafter).
Figure 8B:
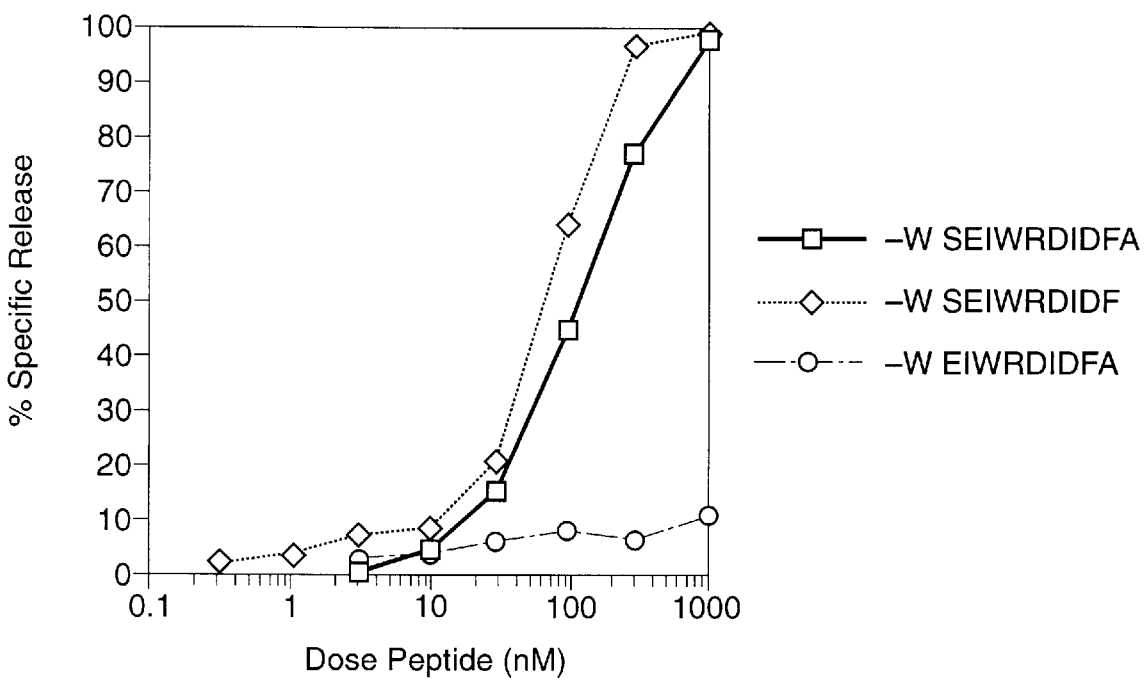

The nonamer:

Glu Ile Trp Arg Asp Ile Asp Phe Ala (SEQ ID NO: 9)

in contrast, was not recognized. Table 7, which follows, summarizes these results, which are also depicted in FIG. 8.

The only other peptide reported to be bound by HLA-B44 is

Glu Glu Asn Leu Leu Asp Phe Val Arg Phe (SEQ ID NO: 10)

as reported by Burrows et al., J. Virol 64: 3974 (1990). The data described supra suggest that Glu at second position and Phe in ninth position may represent anchor residues for HLA-B44.

TABLE 7

10M94-pept tyros on B44

| | 1<br>Effector | 2<br>Dose | 3<br>+W SEQ ID NO: 7 | 4<br>+W SEQ ID NO: 8 | 5<br>+W SEQ ID NO: 9 | 6<br>−W SEQ ID NO: 7 | 7<br>+W SEQ ID NO: 8 | 8<br>+W SEQ ID NO: 9 |
|---|---|---|---|---|---|---|---|---|
| 1 | MZ2-CTL- | 1 μM | 91 | 93 | 7 | 98 | 99 | 11 |
| 2 | 22/31 | 300 nM | 76 | 81 | 4 | 77 | 97 | 6 |
| 3 | 45:1 | 100 | 43 | 73 | 2 | 45 | 64 | 8 |
| 4 | | 30 | 17 | 37 | 0 | 15 | 21 | 6 |
| 5 | | 10 | 4 | 12 | 1 | 5 | 8 | 4 |
| 6 | | 3 | 3 | 4 | 1 | 0 | 7 | 2 |
| 7 | | 1 | 2 | 4 | | | 3 | |
| 8 | | 0.3 | 1 | 1 | | | 2 | |

The foregoing experiments demonstrate that tyrosinase is processed as a tumor rejection antigen precursor, leading to formation of complexes of the resulting tumor rejection antigens with a molecule on at least some abnormal cells, for example, melanoma cells with HLA-A2 or HLA-B44 phenotype. The complex can be recognized by CTLs, and the presenting cell lysed. This observation has therapeutic and diagnostic ramifications which are features of the invention. With respect to therapies, the observation that CTLs which are specific for abnormal cells presenting the aforementioned complexes are produced, suggests various therapeutic approaches. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and are capable of provoking a specific CTL to proliferate. The target cell can be a transfectant, such as a COS cell of the type described supra. These transfectants present the desired complex on their surface and, when combined with a CTL of interest, stimulate its proliferation. So as to enable the artisan to produce these CTLs, vectors containing the genes of interest, i.e., pcDNA-1/Amp1 (HLA-A2), and p123.B2 (human tyrosinase), have been deposited in accordance with the Budapest Treaty at the Institut Pasteur, under Accession Numbers I1275 and I1276, respectively. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present one or more of the HLA/tyrosinase derived peptide complexes. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for their HLA phenotype, using standard assays, and determines expression of tyrosinase via amplification using, e.g., PCR. The fact that a plurality of different HLA molecules present TRAs derived from tyrosinase increases the number of individuals who are suitable subjects for the therapies discussed herein.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining tyrosinase itself with an adjuvant to facilitate incorporation into HLA-A2 presenting cells. The enzyme is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

The invention also provides a method for identifying precursors to CTL targets. These precursors are referred to as tumor rejection antigens when the target cells are tumors, but it must be pointed out that when the cell characterized by abnormality is not a tumor, it would be somewhat misleading to refer to the molecule as a tumor rejection antigen. Essentially, the method involves identifying a cell which is the target of a cytolytic T cell of the type discussed supra. Once such a cell is identified, total RNA is converted to a cDNA library, which is then transfected into a cell sample capable of presenting an antigen which forms a complex with a relevant HLA molecule. The transfectants are contacted with the CTL discussed supra, and again, targeting by the CTL is observed (lysis and/or TNF production). These transfectants which are lysed are then treated to have the cDNA removed and sequenced, and in this manner a precursor for an abnormal condition such as a tumor rejection antigen precursor, can be identified.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. A method for identifying a subject for treatment with a therapeutic agent which is specific for complexes of an MHC molecule and a tyrosinase derived peptide selected from the group consisting of SEQ ID NO: 7, and SEQ ID NO: 8, wherein said complexes are present on surfaces of abnormal cells of said subject, comprising:

(i) contacting a sample containing abnormal cell, which has been taken from said subject, with a cytolytic T cell specific for said complexes, and (ii) determining lysis of at least some of said abnormal cells as an indication that the subject is a candidate for said treatment.

2. The method of claim 1, wherein said MHC molecule is HLA-B44.

3. Isolated cytolytic T cell specific for a complex of an MHC molecule selected from the group consisting of HLA-B44 and a tyrosinase derived peptide selected from the group consisting of SEQ ID NO: 7, and SEQ ID NO: 8.

4. The isolated cytolytic T cell of claim 3, specific for a complex of HLA-B44 and SEQ ID NO: 7.

5. The isolated cytolytic T cell of claim 3, specific for a complex of HLA-B44 and SEQ ID NO: 8.

6. A method for identifying abnormal cells which present complexes of an MHC molecule and a tyrosinase derived peptide selected from the group consisting of SEQ ID NO: 7 and SEQ ID NO; 8 on their surfaces, comprising contacting a sample which contains said abnormal cells with a cytolytic T cell specific for said complexes, and determining lysis of said abnormal cells by said cytolytic T cells as a determination of said abnormal cells.

7. The method of claim 6, wherein said MHC molecule is HLA-B44.

* * * * *

UNITED STATES PATENT AND TRADEMARK OFFICE
CERTIFICATE OF CORRECTION

PATENT NO. : 5,843,687
DATED : Dec. 1, 1998
INVENTOR(S) : Wölfel et al.

It is certified that error appears in the above-identified patent and that said Letters Patent is hereby corrected as shown below:

On the cover page, in the section entitled Other Publications, change "Abstracat" to -- Abstract --.
In column 2, line 17, change "CDNA" to -- cDNA --.
In column 2, line 27, change "patent" to -- Patent --.
In column 2, line 27, change "application" to -- Application --.
In column 5, line 8, change "CDNA" to -- cDNA --.
In column 5, line 64, italicize "supra" to read as -- *supra* --.
In column 6, line 17, change "CDNA" to -- cDNA --.
In column 6, line 37, change "CDNA" to -- cDNA --.
In column 6, line 38, italicize "supra" to read as -- *supra* --.
In column 6, line 39, change "CDNA" to -- cDNA --.
In column 6, line 45, italicize "supra" to read as -- *supra* --.
In column 7, line 12, change "10ox" should read --100 $\lambda$ --.
In column 7, line 35, italicize "supra" to read as -- *supra* --.
In column 7, line 37, italicize "supra" to read as -- *supra* --.
In column 7, line 50-51, change "SK29-CTL IVSB" to -- IVSB --.

UNITED STATES PATENT AND TRADEMARK OFFICE
CERTIFICATE OF CORRECTION

PATENT NO. : 5,843,687
DATED : Dec. 1, 1998
INVENTOR(S) : Wölfel et al.

It is certified that error appears in the above-identified patent and that said Letters Patent is hereby corrected as shown below:

In column 10, line 8, italicize "inter alia" to read as - - *inter alia* - -.
In column 13, line 5, change "CDNA" to - - cDNA - -.
In column 13, line 7, change "CDNA" to - - cDNA - -.
In column 13, line 10, italicize "supra" to read as - - *supra* - -.
In column 13, Table 7, left hand corner, delete "10M94-pept tyros on B44"
In column 13, Table 7, column 1, line 1, change "MZ2-CTL" to
- - MZ2-CTL- 22/31 - -.
In column 13, Table 7, column 1, line 2, delete "22/31".
In column 15, line 13, italicize "in vitro" to read as - - *in vitro* - -.
In column 15, line 43, italicize "supra" to read as - - *supra* - -.
In column 15, line 45, italicize "in vitro" to read as - - *in vitro* - -.
In column 15, line 57, italicize "in vivo" to read as - - *in vivo* - -.
In column 16, line 13, italicize "Vaccina" to read as - - *Vaccina* - -.
In column 16, line 38, italicize "supra" to read as - - *supra* - -.
In column 16, line 43, italicize "supra" to read as - - *supra* - -.

Signed and Sealed this

Thirteenth Day of February, 2001

Attest:

NICHOLAS P. GODICI

Attesting Officer

Acting Director of the United States Patent and Trademark Office